United States Patent [19]

Morita et al.

[11] Patent Number: 5,214,181

[45] Date of Patent: May 25, 1993

[54] AMINO ACID DERIVATIVES

[75] Inventors: Takakazu Morita, Toyonaka; Shiro Mita, Ashiya; Yoichi Kawashima, Kyoto, all of Japan

[73] Assignee: Santen Pharmaceutical Co., Ltd., Osaka, Japan

[21] Appl. No.: 730,832

[22] PCT Filed: Nov. 21, 1990

[86] PCT No.: PCT/JP90/01515

§ 371 Date: Jul. 12, 1991

§ 102(e) Date: Jul. 12, 1991

[87] PCT Pub. No.: WO91/08199

PCT Pub. Date: Jun. 13, 1991

[30] Foreign Application Priority Data

Nov. 27, 1989 [JP] Japan .................... 1-307359

[51] Int. Cl.$^5$ .............. C07C 327/20; C07C 321/22; C07C 329/14
[52] U.S. Cl. .................. 558/248; 558/250; 558/251; 558/254; 560/16; 560/153; 562/426; 562/556; 564/153; 564/154
[58] Field of Search .............. 560/16, 153; 562/426, 562/556; 514/538, 562, 512, 513, 616; 558/251, 254, 248, 250; 564/153, 154

[56] References Cited

U.S. PATENT DOCUMENTS 4,847,200 7/1989 Wolfe et al. .................... 560/16

OTHER PUBLICATIONS

Stedman's Medical Dictionary, 23rd Ed., Williams & Wilkins Company, Baltimore, p. 31, (1970).
Bach, et al., Bulletin de L'Institut Pasteur, 1978, pp. 325–398.
Bach, et al., Med. Oncol. & Tumor Pharmacother, vol. 6, No. 1, pp. 25–29, 1989.
Helv. Chim. Acta, 67 (3), 870–5 (1984), James A. Shields et al.

*Primary Examiner*—Mary C. Lee
*Assistant Examiner*—Joseph K. McKane
*Attorney, Agent, or Firm*—Frishauf, Holtz, Goodman & Woodward

[57] ABSTRACT

This invention relates to novel compounds of the formula [I], which are useful for treatment of various diseases such as immunodeficiency and autoimmune diseases caused by immune disorders, processes for preparing the compounds and compositions containing the compounds as active ingredients.

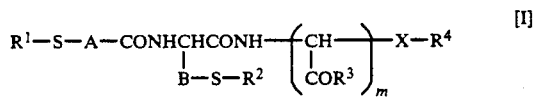

6 Claims, No Drawings

AMINO ACID DERIVATIVES

TECHNICAL FIELD

This invention offers novel compounds which are useful for treatment of various diseases such as immunodeficiency and autoimmune diseases caused by immune disorders.

BACKGROUND ART

Recently there are many studies on mechanisms and therapeutic agents for various diseases caused by immune disorders and immune depression due to side effects of carcinostatic agents. It is known that thymulin, nonapeptide produced in thymus, shows a recovering effect for depressed immunity by conforming a complex with zinc. Therefore, thymulin has a possibility to be applied for treatment of immunodeficiency and autoimmune diseases. But there are many unclear points about the actions of thymulin, and few studies on synthetic compounds showing thymulin-like effects have been made.

Thymulin is a very small amount substance produced in thymus and easily decomposed by enzyme existing in living body because thymulin is a natural product. Therefore, there are many problems to apply thymulin to clinical use. Considering the action mechanism of thymulin, namely thymulin shows effects by conforming a complex with zinc, we synthesized various amino acid derivatives having sulfur atoms and examined the effects thereof comparing with thymulin.

DISCLOSURE OF THE INVENTION

This invention relates to a compound of the formula [I] and salts thereof,

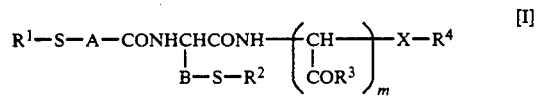

wherein
$R^1$ and $R^2$ are the same or different and each is hydrogen, lower alkyl, lower alkanoyl, phenylcarbonyl, phenyl lower alkyl or phenyl lower alkoxycarbonyl, and said phenyl ring of phenylcarbonyl, phenyl lower alkyl or phenyl lower alkoxycarbonyl can be substituted by lower alkyl, hydroxy, lower alkoxy or halogen;
$R^3$ is hydroxy, lower alkoxy, amino or lower alkylamino;
$R^4$ is hydroxy,

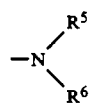

or $-COR^7$;
$R^5$ and $R^6$ are the same or different and each is hydrogen, lower alkyl, lower alkanoyl, lower alkoxycarbonyl, phenylcarbonyl, phenyl lower alkyl, phenyl lower alkoxycarbonyl or

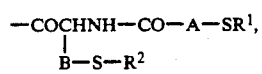

and said phenyl ring of phenylcarbonyl, phenyl lower alkyl or phenyl lower alkoxycarbonyl can be substituted by lower alkyl, hydroxy, lower alkoxy or halogen;
$R^7$ is the same definition as $R^3$;
A, B and X are the same or different and each is straight or branched lower alkylene; and
m is 0 or 1,
the same shall be applied hereinafter.

The terms defined above are explained as follows in more detail.

The term "lower alkyl" intends to designate straight or branched alkyl having 1 to 6 carbon atoms exemplified by methyl, ethyl, propyl, hexyl, isopropyl and t-butyl. The term "lower alkanoyl" intends to designate straight or branched alkanoyl having 2 to 6 carbon atoms exemplified by acetyl, propionyl, hexanoyl, isopropionyl and t-butanoyl. The term "lower alkoxy" intends to designate straight or branched alkoxy having 1 to 6 carbon atoms exemplified by methoxy, ethoxy, propoxy, hexyloxy, isopropoxy and t-butoxy. The term "halogen" intends to designate fluorine, chlorine, bromine and iodine.

The "salt" means a pharmaceutically acceptable salt with organic acid or base, or inorganic acid or base. Examples of such salts are hydrochloric acid salt, hydrobromic acid salt, sulfuric acid salt, phosphoric acid salt, lactic acid salt, maleic acid salt, fumaric acid salt, oxalic acid salt, methanesulfonic acid salt, p-toluenesulfonic acid salt, sodium salt, potassium salt, calcium salt, magnesium salt, zinc salt, ammonium salt, triethanolamine salt and dicyclohexylamine salt.

The compounds of this invention can be prepared by the following methods.

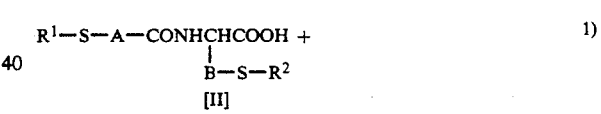

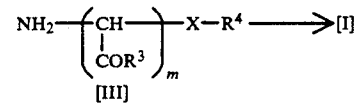

The compound of the formula [II] is condensed with the compound of the formula [III] to give the compound of the formula [I] using a condensing agent such as N,N'-dicyclohexylcarbodiimide which is widely used for peptide synthesis.

b) The compound of the formula [II] is derived to the active derivatives such as acid chloride, acid anhydride, mixed acid anhydride and active ester, and reacted with the compound of the formula [III] to give the compound of the formula [I].

The above methods are widely used for peptide synthesis and it is not necessary to specify the reaction condition.

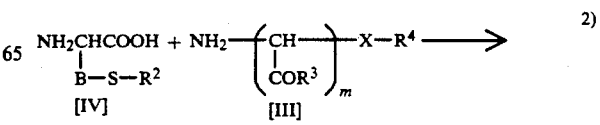

-continued

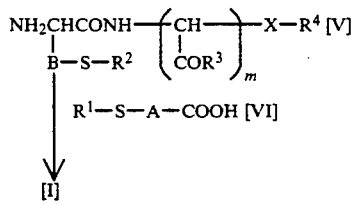

The compound of the formula [I] can be prepared by a reaction of the compound of the formula [V] with the compound of the formula [VI] by the similar method as shown in the part 1).

The compound of the formula [V] can be prepared by a reaction of the compound of the formula [IV] with the compound of the formula [III], in which the amino group of the formula [IV]can be protected with a group widely used for peptide synthesis such as t-butoxycarbonyl group or benzyloxycarbonyl group, and such protective group can be removed after the reaction.

In each compound of the part 1) or 2), when $R^1$, $R^2$, $R^3$ or $R^4$ contains a group exemplified by lower alkanoyl, lower alkoxy, lower alkoxycarbonyl, (substituted) phenylcarbonyl, (substituted) phenyl lower alkyl or (substituted) phenyl lower alkoxycarbonyl, and said group is intended to be used as a protective group, such protective group can be removed during or after the reaction shown in the part 1) or 2).

The compounds prepared by the above methods can be converted into the salts explained before by usual methods.

The compounds of this invention have stereoisomers because of the existence of asymmetric carbon atom(s), and these stereoisomers are included in this invention.

The compound of this invention have thymulin-like activities and are useful for treatment of various diseases such as immunodeficiency and autoimmune diseases which are caused by immune disorders. Thymulin, a very small amount substance produced in thymus, is known to conform a complex with zinc and show a recovering effect for depressed immunity.

However, there are many problems to apply thymulin to clinical use. Therefore, considering the action mechanism of thymulin, we synthesized various amino acid derivatives having sulfur atoms and examined the thymulin-like activities thereof. As the result of our study, we found that the compounds of this invention have excellent thymulin-like activities, the details are shown in the article of pharmacological test, and are useful for treatment of various diseases such as immunodeficiency and autoimmune diseases which are caused by immune disorders There are various diseases caused by immune disorders, and examples of such diseases are rheumatoid arthritis, chronic hepatitis, anemia, systemic lupus erythematosus, primary immunodeficiency and agamma-globulinemia. The compound of this invention are useful for treatment of such diseases.

It is considered that the compounds of this invention show the activities, like thymulin by conforming a complex with zinc. In a clinical use, zinc existing in human body in a very small amount may be used to conform a complex with the compounds of the invention to show the activities, of cause the compounds of this invention can be jointly used with zinc salt such as zinc chloride.

The compounds of this invention can be administered either orally or parenterally. Examples of dosage forms are tablet, capsule and injection. The preparations can be prepared by usual methods. The dosage is adjusted depending on symptom, dosage form, etc. and should not be restricted in specific range.

BEST MODE TO MAKE THE INVENTION

Example 1

N-[S-benzyl-N-(3-benzylthio-2,2-dimethylpropionyl)-D-cysteinyl]glycine ethyl ester (compound No. 1)

To a stirred solution of S-benzyl-N-(3-benzylthio-2,2-dimethyl-propionyl)-D-cysteine (0.32g) and glycine ethyl ester hydro-chloride (0.12g) in N,N-dimethylformamide (DMF, 3ml), N-methylmorpholine (NMM, 0.19ml), 1-hydroxybenzotriazole (HOBt, 0.17g) and then a solution of N,N,-dicyclohexylcarbodiimide (DCC, 0.18g) in DMF (2 ml) were added under ice cooling. The mixture was stirred for 2hr. at 0° C. and for 2 hr. at room temperature, and stood overnight. 1N hydrochloric acid (30 ml) was added into the reaction mixture and the mixture was extracted with ether. The organic layer was washed with saturated sodium bicarbonate solution and saturated sodium chloride solution, dried over anhydrous sodium sulfate, and concentrated in vacuo. The oily residue was purified by a silica gel column chromatography to give 0.35 g (91%) of the titled compound.

IR (film, cm$^{-1}$): 1745, 1741, 1634, 1519, 1508, 1493, 1451, 1374, 1196, 700

$[\alpha]^{20}_D$ +28.2° (c=1.3, methanol)

Example 2

N-[S-benzyl-N-(3-benzylthio-2,2-dimethylpropionyl)-D-cysteinyl]-glycinamide (compound No.2)

Ammonia gas was bubbled for 15 minutes into a solution of compound No. 1 (1.85 g) in methanol (50 ml) and the reaction mixture was stood overnight. The reaction mixture was concentrated in vacuo to give 1.75g ( quantitative yield ) of the titled compound.

IR (KBr, cm$^{-1}$): 1673, 1624, 1528, 1493, 1383, 1231, 1223, 696

Example 3

N-[N-(2,2-dimethyl-3-mercaptopropionyl)-D-cysteinyl]glycinamide (compound No. 3)

To a solution of compound No.2 (1.60 g) in liquid ammonia (20 ml), sodium metal (0.45 g) was added in a small portion under nitrogen atmosphere. After an addition of ammonium chloride, ammonia was evaporated. 2N hydrochloric acid was added to the residue and acidified, and the mixture was extracted with ether. The organic layer was dried over anhydrous sodium sulfate and concentrated in vacuo. The oily residue was purified by a silica gel column chromatography to give 0.58g (59%) of the titled compound.

IR (film, cm$^{-1}$) 3304, 2540, 1654, 1644, 1634, 1513, 1474, 1418, 1388, 1234, 558

$[\alpha]^{20}_D$ +18.9. (c=1.2, methanol)

By the similar method as Example 3, following compounds were obtained.

N,N'-bis[N-(2,2-dimethyl-3-mercaptopropionyl)-L-cysteinyl]-1,5-diaminopentane (compound No. 4)

N,N'-bis[S-benzyl-N-(3-benzylthio-2,2-dimethylpropionyl)-L-cysteinyl]-1,5-diaminopentane (compound No. 32) was used as a starting material.

IR (nujol, cm$^{-1}$): 3300, 2924, 1653, 1522, 1458, 1376, 720

$[\alpha]^{20}{}_D$ −27.6° (c=1.0, methanol)

3-Amino-N-[N-(2,2-dimethyl-3-mercaptopropionyl)-L-cysteinyl]propylamine hydrochloride (compound No. 5)

3-Amino-N-[S-benzyl-N-(3-benzylthio-2,2-dimethylpropionyl)-L-cysteinyl]propylamine (compound No. 28) was used as a starting material.

IR (nujol, cm$^{-1}$): 3236, 2920, 1641, 1515, 1468, 1365, 1240

$[\alpha]^{20}{}_C$ −19.9° (c=1.0, methanol)

4-Amino-N-[N-(2,2-dimethyl-3-mercaptopropionyl)-L-cysteinyl]butylamine hydrochloride (compound No. 6)

4-Amino-N-[S-benzyl-N-(3-benzylthio-2,2-dimethylpropionyl)L-cysteinyl]butylamine (compound No.29 ) was used as a starting material.

IR (nujol, cm$^{-1}$): 3240, 2916, 1640, 1513, 1469, 1365, 1229

$[\alpha]^{20}{}_D$ −13.1° (c=0.9, methanol)

5-Amino-N-[N-(2,2-dimethyl-3-mercaptopropionyl)-L-cysteinyl]pentylamine hydrochloride (compound No. 7)

5-Amino-N-[S-benzyl-N-(3-benzylthio-2,2-dimethylpropionyl)-L-cysteinyl]pentylamine (compound No. 31) was used as a starting material.

IR (nujol, cm$^{-1}$) 3260, 2945, 1648, 1519, 1484, 1370, 1232

$[\alpha]^{20}{}_D$ −16.6° (c=1.0, methanol)

6-Amino-N-[N-(2,2-dimethyl-3-mercaptopropionyl)-L-cysteinyl]hexylamine hydrochloride (compound No. 8)

6-Amino-N-[S-benzyl-N-(3-benzylthio-2,2-dimethylpropionyl)-L-cysteinyl]hexylamine (compound No. 30) was used as a starting material.

IR (KBr, cm$^{-1}$) 3260, 2928, 1639, 1517, 1468, 1364, 1229

$[\alpha]^{20}{}_D$ 14.2° (c=1.0, methanol)

5-Hydroxy-N-[N-(2,2-dimethyl-3-mercaptopropionyl)-L-cysteinyl]pentylamine (compound No. 9)

5-Hydroxy-N-[S-benzyl-N-(3-benzylthio-2,2-dimethylpropionyl)-L-cysteinyl]pentylamine (compound No. 33 ) was used as a starting material.

IR (film, cm$^{-1}$): 3312, 2936, 1638, 1530, 1473, 1365, 1239

$[\alpha]^{20}{}_D$ 14.0 (c=1.0, methanol)

Example 4

N$^\alpha$[S-benzyl-N-(3-benzylthio-2,2-dimethylpropionyl)-L-cysteinyl]-N$^\epsilon$-t-butoxycarbonyl-L-lysine methyl ester (compound No. 10)

To a stirred solution of S-benzyl-N-(3-benzylthio-2,2-dimethylpropionyl)-L-cysteine (4.01 g), N$^\epsilon$-t-butoxycarbonyl-Llysine methyl ester (2.08 g) and NMM (1.1 ml) in DMF (20ml), HOBt (2.16 g) and then a solution of DCC (1.82g) in DMF (10ml) were added slowly under ice cooling. The mixture was stirred for 1 hr. under ice cooling and for 18hr. at room temperature. After an addition of a mixture of ethyl acetate and benzene ( 2:1, 500 ml ), the mixture was washed with 10% citric acid solution, water, saturated sodium bicarbonate solution, water and then saturated sodium chloride solution. The organic layer was dried over anhydrous sodium sulfate and concentrated in vacuo. The oily residue was purified by a silica gel column chromatography to give 3.22g (61%) of the titled compound.

IR (film, cm$^{-1}$): 3300, 2928, 1741, 1682, 1639, 1509, 1364, 1244, 1194, 701

$[\alpha]^{25}{}_D$ −17.7° (c=1.0, methanol)

Example 5

N$^\alpha$-[S-benzyl-N-(3-benzylthio-2,2-dimethylpropionyl)-L-cysteinyl]-N$^\epsilon$-t-butoxycarbonyl-L-lysine (compound No. 11)

To a solution of compound No.10 (2.21g) in a mixture of dioxane and methanol (35ml), 1N sodium hydroxide solution (8ml) was added under ice cooling and the mixture was stirred for 1.5 hr. at room temperature. After an addition of dilute hydrochloric acid for acidification, sodium chloride was added into the reaction mixture and the mixture was extracted with ethyl acetate. The organic layer was dried over anhydrous sodium sulfate and concentrated in vacuo. The oily residue was purified by a silica gel column chromatography to give 1.98g (92%) of the titled compound.

IR (film, cm$^{-}$:): 3312, 2964, 2924, 1701, 1635, 1513, 1365, 1243, 1167, 701

$[\alpha]^{25}{}_D$ −14.1 (c=1.0, methanol)

By the similar method as Example 5, following compounds were obtained.

N$^\alpha$-[S-benzyl-N-(3-benzylthio-2,2-dimethylpropionyl)-L-cysteinyl]-N$^\epsilon$-benzyloxycarbonyl-L-lysine (compound No. 12)

N$^\epsilon$-[S-benzyl-N-(3-benzylthio-2,2-dimethylpropionyl)-L-cysteinyl]-N$^\epsilon$-benzyloxycarbonyl-L-lysine methyl ester (compound No. 20) was used as a starting material.

(KBr, cm$^{-1}$): 3344, 3000, 2928, 1717, 1672, 1509, 1497, 1206, $[\alpha]^{20}{}_D$ −30.0° (c=1.01, methanol)

Data of dicyclohexylamine salt of the titled compound
  m.p. 117-118° C. (ethyl acetate - n-hexane)

IR (KBr, cm$^{-1}$): 3332, 2932, 2320, 1691, 1634, 1576, 1523, 1508, 1497, 698

$[\alpha]^{20}{}_D$ −22.0° (c=1.10, methanol)

N$^\alpha$-[S-benzyl-N-[2,2-dimethyl-3-(4-methoxybenzylthio)propionyl]-L-cysteinyl]-N$^\epsilon$-benzyloxycarbonyl-L-lysine (compound No. 13)

N$^\alpha$-[S-benzyl-N-[2,2-dimethyl-3-(4-methoxybenzylthio)propionyl]-L-cysteinyl]-N$^\epsilon$-benzyloxycarbonyl-L-lysine methyl ester (compound No. 19) was used as a starting material.

IR (CHCl$_3$, cm$^{-1}$): 2928, 1715, 1667, 1512, 1234, 1206, 717

$[\alpha]^{20}{}_D$ −29.3° (c=1.01, methanol)

N$^\alpha$-[S-benzyl-N-(2-benzylthio-2-methylpropionyl)-L-cysteinyl]-N$^\epsilon$-benzyloxycarbonyl-L-lysine (compound No. 14 )

N$^\alpha$-[S-benzyl-N-(2-benzylthio-2-methylpropionyl)-L-cysteinyl]-N$^\epsilon$-benzyloxycarbonyl-L-lysine methyl ester (compound No. 18) was used as a starting material.

IR (CHCl$_3$, cm$^{-1}$): 3344, 1716, 1667, 1508, 1497, 1205, 697

$[\alpha]^{20}{}_D$ −17.6° (c=0.67, methanol)

Data of dicyclohexylamine salt of the titled compound
  m.p. 108-110° C. (ethyl acetate - n-hexane)

IR (KBr, cm$^{-1}$): 3352, 2936, 2860, 1690, 1635, 1535, 1492, 1268, 697

$[\alpha]^{20}_D -13.8°$ (c = 1.0, methanol)

N-[S-benzyl-N-(3-benzylthio-2,2-dimethylpropionyl)-D-cysteinyl]-glycine (compound No. 15)

N-[S-benzyl-N-(3-benzylthio-2,2-dimethylpropionyl)-D-cysteinyl]glycine ethyl ester (compound No.1) was used as a starting material.

IR (film, cm-:): 3328, 1729, 1643, 1532, 1496, 1453, 1208, 702

$[\alpha]^{20}_D +28.1°$ (c = 1.0, methanol)

Example 6

N$^\alpha$-[N-(2,2-dimethyl-3-mercaptopropionyl)-L-cysteinyl]-N$^\epsilon$-t-butoxycarbonyl-L-lysine (compound No. 16)

A solution of compound No.11 (3.83g) in dry tetrahydrofuran (THF, 20 ml) was added to liquid ammonia (70 ml). To the solution, sodium metal was added in a small portion until blue coloring of the solution maintained for one minute. After an addition of ammonium chloride to the reaction mixture, ammonia was removed by blowing nitrogen gas, and the resulting mixture was further concentrated. The white residue was dissolved in a mixture of ethyl acetate (200ml) and 10% citric acid solution (50 ml). After an addition of sodium chloride to the solution, the organic layer was separated and dried over anhydrous sodium sulfate, and concentrated in vacuo. The oily residue was purified by a silica gel column chromatography to give 0.58g (65%) of the titled compound as white powders.

IR (KBr, cm$^{-1}$): 3288, 2916, 1636, 1509, 1164

$[\alpha]^{25}_D -4.2°$ (c = 1.0, methanol)

Example 7

N$^\alpha$-[N-(2,2-dimethyl-3-mercaptopropionyl)-L-cysteinyl]-L-lysine methyl ester hydrochloride (compound No. 17)

Compound No.16 (1.03 g) was dissolved in 4N hydrogen chloride methanol (10 ml), and the mixture was stirred for 30 minutes at room temperature and then concentrated in vacuo. The oily residue was purified by a silica gel column chromatography to give 0.58 g (65%) of the titled compound as white powders.

IR (KBr, cm$^{-1}$): 3204, 2920, 1732, 1634, 1508, 1207

$[\alpha]^{25}_D -17.3°$ (c = 1.0, methanol)

Example 8

N$^\alpha$-[S-benzyl-N-(2-benzylthio-2-methylpropionyl)-L-cysteinyl]-N$^\epsilon$-benzyloxycarbonyl-L-lysine methyl ester (compound No. 18)

To stirred a solution of N$^\alpha$-(S-benzyl-L-cysteinyl)-N$^\epsilon$-benzyloxycarbonyl-L-lysine methyl ester hydrochloride (3.1 g) in DMF (15 ml), NMM (1.2 g), 2-benzylthio-2-methylpropionic acid (1.36 g), HOBt (1.6 g) and then a solution of DCC (1.34 g) in DMF (5 ml) were added dropwise under nitrogen atmosphere and ice cooling, and the mixture was stirred for 1hr. under ice cooling, and for 16 hr. at room temperature. The mixture was filtered and the filtrate was concentrated in vacuo, and the residue was dissolved in a mixture of ethyl acetate and benzene (2:1, 300ml). The solution was washed with 10% citric acid solution, water, 5% sodium bicarbonate solution, water and then saturated sodium chloride solution, dried over anhydrous sodium sulfate, and concentrated in vacuo. The oily residue was purified by a silica gel column chromatography to give 4.2g (98%) of the titled compound.

IR (KBr, cm$^{-1}$): 3312, 1744, 1686, 1637, 1547, 1496, 1252, 699

$[\alpha]^{20}_D 20.9°$ (c = 0.53, methanol)

By the similar method as Example 8, following compounds were obtained.

N$^\alpha$-[S-benzyl-N-[2,2-dimethyl-3-(4-methoxybenzylthio)propionyl]-L-cysteinyl]-N$^\epsilon$-benzyloxycarbonyl-L-lysine methyl ester (compound No. 19)

N$^\alpha$-(S-benzyl-L-cysteinyl)-N -benzyloxycarbonyl-L-lysine methyl ester hydrochloride and 2,2-dimethyl-3-(4-methoxybenzylthio)propionic acid were used as starting materials.

IR (film, cm$^{-1}$): 3310, 1738, 1697, 1643, 1510, 1244, 751

$[\alpha]^{20}_D -31.0°$ (c = 1.08, methanol)

N$^\alpha$-[S-benzyl-N-(3-benzylthio-2,2-dimethylpropionyl)-L-cysteinyl]-N$^\epsilon$-benzyloxycarbonyl-L-lysine methyl ester (compound No. 20)

N$^\alpha$-(S-benzyl-L-cysteinyl)-N -benzyloxycarbonyl-L-lysine methyl ester hydrochloride and 3-benzylthio-2,2-dimethylpropionic acid were used as starting materials.

IR (film, cm$^{-1}$): 3316, 2948, 1741, 1697, 1644, 1522, 1454, 1242, 1212, 752, 700

$[\alpha]^{20}_D 30.9°$ (c = 1.01, methanol)

Example 9

N$^\alpha$-[N-(2,2-dimethyl-3-mercaptopropionyl)-L-cysteinyl]-L-lysine (compound No. 21)

A solution of compound No.12 (0.34g) in THF (5ml) was added to liquid ammonia, and sodium metal was added in a small portion to the mixture. After a termination of the reaction, sodium chloride was added to the solution, and then ammonia and THF was evaporated in vacuo. Acetic acid was added and acidified, and the mixture was concentrated in vacuo. The oily residue was purified by a silica gel column chromatography to give 0.17 g (47%) of the titled compound.

IR (KBr, cm$^{-1}$) 3304, 3044, 2928, 2864, 1642, 1523, 1395

$[\alpha]^{20}_D -26.1°$ (c = 1.01, methanol)

By the similar method as Example 9, following compounds were obtained.

N$^\epsilon$,N$^\epsilon$-dimethyl-N$^\alpha$-[N-(2,2-dimethyl-3-mercaptopropionyl)-L-cysteinyl]-L-lysine (compound No. 22)

N$^\alpha$-[S-benzyl-N-(3-benzylthio-2,2-dimethylpropionyl)-L-cysteinyl]-N$^\epsilon$,N$^\epsilon$-dimethyl-L-lysine hydrochloride (compound No. 25) was used as a starting material.

IR (CHCl$_3$, cm$^1$): 2960, 2928, 1648, 1497, 1261, 1095, 1011, 807, 725

$[\alpha]^{20}_D -19.5°$ (c = 1.1, methanol)

N$^\alpha$-[N-(2-mercapto-2-methylpropionyl)-L-cysteinyl]-L-lysine (compound No. 23)

N$^\alpha$-[S-benzyl-N-(2-benzylthio-2-methylpropionyl)-L-cysteinyl]-N$^\epsilon$-benzyloxycarbonyl-L-lysine (compound No. 14) was used as a starting material.

IR (KBr, cm$^{-1}$) 3336, 2920, 2856, 1648, 1577, 1509, 1458, 1394

$[\alpha]^{20}_D -11.7°$ (c = 1.0, methanol)

Example 10

N$^\alpha$-[S-benzyl-N-(3-benzylthio-2,2-dimethylpropionyl)-L-cysteinyl]-L-lysine hydrobromide (compound No. 24)

To a solution of compound No. 12 (2.14g) in acetic acid (35 ml), 25% hydrobromide / acetic acid solution (10 ml) was added under ice cooling, and the mixture was stirred for 50 minutes at room temperature. The mixture was concentrated in vacuo and the oily residue was purified by a silica gel column chromatography to give 1.83g (93%) of the titled compound.

IR (CHCl$_3$, cm$^{-1}$): 2964, 2924, 1727, 1642, 1508, 1496, 1454, 1205, 699

$[\alpha]^{20}_D$ —32.0° (c=1.0, methanol)

Example 11

N$^\alpha$-[S-benzyl-N-(3-benzylthio-2,2-dimethylpropionyl)-L-cysteinyl]-N$^\epsilon$,N$^\epsilon$-dimethyl-L-lysine hydrochloride (compound No. 25)

To a solution of compound No.24 (0.8g) in methanol (25 ml), 37% formalin solution (1ml) was added and the mixture was stirred for 10 minutes under ice-methanol cooling. To the mixture, sodium borohydride (0.45g) was added in a portion and the mixture was stirred for 30 minutes. Dilute hydrochloric acid was added and acidified, and the mixture was concentrated in vacuo and extracted with chloroform. The solvent was removed in vacuo and the oily residue was purified by a silica gel column chromatography to give 0.58g (81%) of the titled compound.

IR (CHCl$_3$, cm$^{-1}$): 2956, 2928, 2860, 1731, 1661, 1507, 1496, 1477, 1465, 1205, 700

$[\alpha]^{20}_D$ —29.6° (c=1.0, methanol)

Example 12

N$^\alpha$-[S-acetyl-N-(3-acetylthio-2,2-dimethylpropionyl)-L-cysteinyl]-N$^\epsilon$-t-butoxycarbonyl-L-lysine (compound No. 26)

To a solution of compound No. 16 (0.79g) in 1N sodium hydroxide solution (5.5 ml), acetyl chloride (0.43 g) dissolved in methylene chloride (6 ml) was added with vigorous stirring under nitrogen atmosphere and ice cooling. The mixture was stirred for 1.5 hr. and extracted with methylene chloride (30 ml). To the organic layer, triethylamine (0.2ml) was added, and then iodine dissolved in methylene chloride was added until the reaction mixture began to be colored. The mixture was concentrated in vacuo and the oily residue was purified by a silica gel column chromatography to give 0.664g (71%) of the titled compound.

IR (film, cm$^{-1}$): 3324, 2972, 2932, 1692, 1650, 1518, 1366, 1246, 1168, 1133, 624

$[\alpha]^{20}_D$ 8.4° (c=1.3, methanol)

Example 13

N$^\alpha$-[S-acetyl-N-(3-acetylthio-2,2-dimethylpropionyl)-L-cysteinyl]-L-lysine methyl ester hydrochloride (compound No. 27)

To a solution of compound No.26 (0.344 g) in methanol (10 ml), 6.5N hydrogen chloride / dioxane (0.3 ml) was added and the mixture was stirred for 1 hr. at room temperature. The mixture was concentrated in vacuo and the oily residue was purified by a silica gel column chromatography to give 0.25g (79%) of the titled compound.

IR (CHCl$_3$, cm$^{-1}$) 2956, 1745, 1690, 1647, 1517, 1220, 1135, 625

$[\alpha]^{20}_D$ —16.4° (c=1.0, methanol)

Example 14

3-Amino-N-[S-benzyl-N-(3-benzylthio-2,2-dimethylpropionyl)-L-cysteinyl]propylamine (compound No. 28)

To a stirred solution of S-benzyl-N-(3-benzylthio-2,2-dimethylpropionyl)-L-cysteine (2.04 g) and N-hydroxysuccinimide (0.563g) in DMF (5ml), DCC (1.11 g) dissolved in DMF (5 ml) was added dropwise. The mixture was stirred for 0.5 hr. under ice cooling and for 0.5 hr. at room temperature, and filtered. To the filtrate, 1,3-Diaminopropane (1.09g) dissolved in DMF (30 ml) was added dropwise with stirring. The mixture was stirred for 1hr and water was added to the mixture, and then the mixture was extracted with ethyl acetate. The organic layer was washed with water and saturated sodium chloride, dried over anhydrous magnesium sulfate, and concentrated in vacuo. The oily residue was purified by a silica gel column chromatography to give 1.6g (69%) of the titled compound.

IR (film, cm$^{-1}$): 3296, 2924, 1644, 1532, 1496, 1453, 702

$[\alpha]^{20}_D$ —15.8° (c=1.0, methanol)

By the similar method as Example 14, following compounds were obtained.

4-Amino-N-[S-benzyl-N-(3-benzylthio-2,2-dimethylpropionyl)-L-cysteinyl]butylamine (compound No. 29)

S-benzyl-N-(3-benzylthio-2,2-dimethylpropionyl)-L-cysteine and 1,4-diaminobutane were used as starting materials.

IR (film, cm$^{-1}$): 3296, 2928, 1641, 1523, 1496, 1453, 702

$[\alpha]^{20}_D$ —12.6° (c=1.0, methanol)

6-Amino-N-[S-benzyl-N-(3-benzylthio-2,2-dimethylpropionyl)-L- (-) cysteinyl]hexylamine (compound No. 30)

S-benzyl-N-(3-benzylthio-2,2-dimethylpropionyl)-L-cysteine and 1,4-diaminohexane were used as starting materials.

IR (film, cm$^{-1}$) 3296, 2928, 1639, 1531, 1496, 1453, 701

$[\alpha]^{20}_D$ —15.1° (c=1.0, methanol)

Example 15

5-Amino-N-[S-benzyl-N-(3-benzylthio-2,2-dimethylpropionyl)-L-cysteinyl]pentylamine (compound No. 31) and N,N'-bis[S-benzyl-N-(3-benzylthio-2,2-dimethylpropionyl)-L-cysteinyl]-1,5-diaminopentane (compound No. 32)

To stirred a solution of S-benzyl-N-(3-benzylthio-2,2-dimethylpropionyl)-L-cysteine (0.627g) in DMF (5ml), N-hydroxysuccinimide (0.173 g) was added, and then DCC dissolved in DMF (5 ml) was added to the mixture under ice cooling. The mixture was stood overnight under ice cooling and filtered. To the filtrate, water and ethyl acetate was added, and the organic layer was washed with water and saturated sodium chloride solution, dried over anhydrous magnesium sulfate, and concentrated in vacuo. The oily residue was dissolved in chloroform (10 ml), and 1,5-diaminopentane (0.46 g) dissolved in chloroform (10 ml) was added to the solution. The mixture was stirred for 1hr. at room temperature. Water was added to the reaction mixture, and the organic layer was washed with saturated sodium bicarbonate solution and saturated sodium chloride solution, dried over anhydrous magnesium sulfate, and concentrated in vacuo. The oily residue was purified by a silica gel column chromatography to give 0.372g (49%) of compound No. 31 and 0.254 g (38%) of compound No. 32.

Data of compound No. 31

IR (film, cm$^{-1}$): 3292, 2928, 1641, 1533, 1496, 1453, 701

$[\alpha]^{20}_D$ −17.0° (c=1.1, methanol)

Data of compound No. 31

IR (film, cm$^{-1}$) 3308, 2932, 1643, 1530, 1495, 1453, 702

$[\alpha]^{20}_D$ 19.0° (c=1.1, methanol)

Example 16

5-Hydroxy-N-[S-benzyl-N-(3-benzylthio-2,2-dimethyl-propionyl)-L-cysteinyl]pentylamine (compound No. 33)

To a stirred solution of S-benzyl-N-(3-benzylthio-2,2-dimethyl-propionyl)-L-cysteine (4.18 g) and N-hydroxysuccinimide (1.15 g) in DMF (10 ml), DCC (2.06 g) dissolved in DMF (10 ml) was added dropwise under ice cooling and the mixture was stood overnight. The mixture was filtered and 5-aminopentanol (1.55 g) dissolved in DMF (30ml) was added to the filtrate. The mixture was stirred for 3hr. at room temperature. Water was added to the reaction mixture and the mixture was extracted with ethyl acetate. Ethyl acetate layer was washed with saturated sodium bicarbonate solution, water and then saturated sodium chloride solution, dried over anhydrous magnesium sulfate, and concentrated in vacuo. The oily residue was purified by a silica gel column chromatography to give 3.4g (69%) of the titled compound.

IR (film, cm$^{-1}$): 3300, 2928, 1636, 1528, 1494, 1453, 700

$[\alpha]^{20}_D$ −14.6° (c=1.0, methanol)

PHARMACOLOGICAL TEST

Thymulin-like activities of the compounds of this invention were examined by modifying the method reported by J. F. Bach et al. (Bull. Inst. Pasteur, 76, 325 (1978)).

Experimental Method

A thymus of C57BL/6 strain male mouse (10 weeks age, 4 mice a group) was removed. After about two weeks, a spleen of the mouse was extracted and a spleen cells suspension (1×10$^8$ cells/ml in Hank's solution) was prepared. To 100 μl of the cells suspension, 100 μl of Hank's solution dissolving a test compound and zinc chloride in 1:1 molar ratio was added. After a 30 minutes incubation at 37° C., 50 μl of azathiopurine 50 μg/ml in Hank's solution) was added and the mixture was incubated further 60 minutes at the same temperature. To the mixture, 50 μl of sheep red blood cells (1×10$^8$ cells/ml in Hank's solution) was added and mixed. The mixture was incubated at 4° C. for one night. After gently shaking, E-rosette forming cells (E-RFC) were measured. As an active control, a solution of thymulin and zinc chloride, which were dissolved in Hank's solution in a concentration of 1×10$^{-14}$ M and 1:1 molar ratio, was used and it was treated by the same manner as the case of the test compound.

Result

Thymulin-like activities were measured by the following formula.

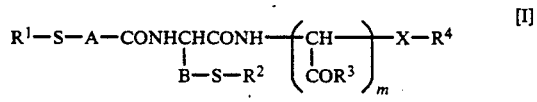

Some of the test results, in which a compound of this invention is added in a concentration of 10$^{-9}$ M, are shown in the following table.

| compound No. | relative activity (%) |
|---|---|
| 4 | 75.5 |
| 5 | 67.2 |
| 6 | 67.2 |
| 7 | 71.9 |
| 8 | 59.8 |
| 9 | 59.8 |
| 17 | 58.1 |
| 21 | 67.1 |
| 23 | 78.3 |

As shown in the table, the compounds of this invention show thymulin-like activities. The results prove the utilities of the compounds of this invention.

What we claim is:

1. A compound of the formula [I] and salts thereof, $$R^1-S-A-CONHCHCONH-\left(CH-\right)_m-X-R^4 \quad [I]$$
$$\overset{|}{B-S-R^2} \quad \overset{|}{COR^3}$$

wherein

R$^1$ and R$^2$ are the same or different and each is hydrogen, lower alkyl, lower alkanoyl, phenylcarbonyl, phenyl lower alkyl or phenyl lower alkoxycarbonyl, and said phenyl ring of phenylcarbonyl, phenyl lower alkyl or phenyl lower alkoxycarbonyl can be substituted by lower alkyl, hydroxy, lower alkoxy or halogen;

R$^3$ is hydroxy, lower alkoxy, amino or lower alkylamino;

R$^4$ is hydroxy,

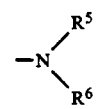

or —COR$^7$;

R$^5$ and R$^6$ are the same or different and each is hydrogen, lower alkyl, lower alkanoyl, lower alkoxycarbonyl, phenylcarbonyl, phenyl lower alkyl, phenyl lower alkoxycarbonyl or

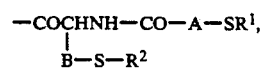

and said phenyl ring of phenylcarbonyl, phenyl lower alkyl or phenyl lower alkoxycarbonyl can be substituted by lower alkyl, hydroxy, lower alkoxy or halogen;

R$^7$ is the same definition as R$^3$;

A, B and X are the same or different and each is straight or branched lower alkylene; and m is 0 or 1.

2. A compound of the formula [II] and salts thereof,

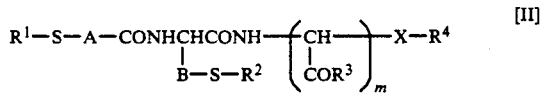

wherein

R¹ and R² are the same or different and each is hydrogen, lower alkanoyl or phenyl lower alkyl which can be substituted by lower alkoxy;

R³ is hydroxy or lower alkoxy;

R⁴ is hydroxy,

or —COR⁷;

R⁵ and R⁶ are the same or different and each is hydrogen, lower alkyl, lower alkoxycarbonyl, phenyl lower alkoxycarbonyl or

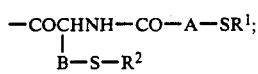

R⁷ is hydroxy, lower alkoxy or amino;

A, B and X are the same or different and each is straight or branched lower alkylene; and m is 0 or 1.

3. A compound of the formula [III] and salts thereof,

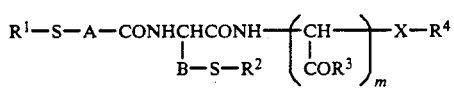

wherein

R¹ and R² are the same or different and each is hydrogen, acetyl, benzyl or methoxybenzyl;

R³ is hydroxy or methoxy;

R⁴ is hydroxy,

or —COR⁷;

R⁵ and R⁶ are the same or different and each is hydrogen, methyl, t-butoxycarbonyl, benzyloxycarbonyl or

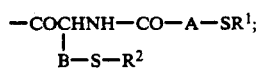

R⁷ is hydroxy, ethoxy or amino;

A, B and X are the same or different and each is straight or branched lower alkylene; and m is 0 or 1.

4. The compound of claim 1, wherein the compound is
N$^\alpha$-(N-2,2-dimethyl-3-mercaptopropionyl)-L-cysteinyl)-L-lysine methyl ester hydrochloride.

5. The compound of claim 1, wherein the compound is selected from the group consisting of
N-(N-(2,2-dimethyl-3-mercaptopropionyl)-D-cysteinyl)glysinamide,
N-N'-bis(N-(2,2-dimethyl-3-mercaptopropionyl)-L-cysteinyl)-1,5-diemainophentane,
3-amino-N-(N-(2,2-dimethyl-3-mercaptopropionyl)-L-cysteinyl)-propylamine hydrochloride,
4-amino-N-(N-(2,2-dimethyl-3-mercaptopropionyl)-L-cysteinyl)-butylamine hydrochloride,
5-amino-N-(N-(2,2-dimethyl-3-mercaptopropionyl)-L-cysteinyl)-pentylamine,
6-amino-N-(N-(2,2-dimethyl-3-mercaptopropionyl)-L-cysteinyl)-hexylamine hydrochloride,
5-hydroxy-N-(N-(2,2-dimethyl-3-mercaptopropionyl)-L-cysteinyl)-pentylamine,
N$^\alpha$-N-(N-(2,2-dimethyl-3-mercaptopropionyl)-L-cysteinyl)-N$^\epsilon$-t-butoxycarbonyl-L-lysine,
N$^\alpha$-(N-(2,2-dimethyl-3-mercaptopropionyl)-L-cysteinyl)-L-lysine,
N$^\epsilon$,N$^\epsilon$-dimethyl-N$^\alpha$-(N-(2,2-dimethyl-3-mercaptopropionyl)-L-cysteinyl)-L-lysine and
N$^\alpha$-(N-2-mercapto-2-methylpropionyl)-L-cysteinyl)-L-lysine.

6. The compound of claim 1, wherein the compound is selected from the group consisting of
N-(S-benzyl-N-(3-benzylthio-2,2-dimethylpropionyl)-D-cysteinyl)-glycine ethyl ester,
N-(S-benzyl-N-(3-benzylthio-2,2-dimethylpropionyl)-D-cysteinyl)-glycinamide,
N$^\alpha$-(S-benzyl-N-(3-benzylthio-2,2-dimethylpropionyl)-L-cysteinyl)-N$^\epsilon$-t-butoxycarbonyl-L-lysine methyl ester,
N$^\alpha$-(S-benzyl-N-(3-benzylthio-2,2-dimethylpropionyl)-L-cysteinyl)-N$^\epsilon$-t-butoxycarbonyl-L-lysine,
N$^\alpha$-(S-benzyl-N-(3-benzylthio-2,2-dimethylpropionyl)-L-cysteinyl)-N$^\epsilon$-benzyloxycarbonyl-L-lysine,
N$^\alpha$-(S-benzyl-N-(2,2-dimethyl-3-(4-methoxybenzylthio)propionyl)-L-cysteinyl)-N$^\epsilon$-benzyloxycabonyl-L-lysine,
N-(S-benzyl-N-(3-benzylthio-2,2-dimethylpropionyl)-D-cysteinyl)-glycine,
N$^\alpha$-(N-(2,2-dimethyl-3-mercaptopropionyl-L-cysteinyl)-L-lysine methyl ester hydrochloride,
N$^\alpha$-(S-benzyl-N-(2-benzylthio-2-methylpropionyl)-L-cysteinyl)-N$^\epsilon$-benzyloxycarbonyl-L-lysine methyl ester,
N$^\alpha$-(S-benzyl-N-(2,2-dimethyl-3-(4-methoxybenzylthio)proionyl)-L-cysteinyl)-N$^\epsilon$-benzyloxycarbonyl-L-lysine methyl ester,
N$^\alpha$-(S-benzyl-N-(3-benzylthio-2,2-dimthylpropionyl)-L-cysteinyl)-N$^\epsilon$-benzyloxycarbonyl-L-lysine methyl ester,
N$^\alpha$-(S-benzyl-N-(3-benzylthio-2,2-dimethylpropionyl)-L-cysteinyl)-L-lysine hydrobromide,
N$^\alpha$-(S-benzyl-N-(3-benzylthio-2,2-dimethylpropionyl)-L-cysteinyl)-N$^\epsilon$,N$^\epsilon$-dimethyl-L-lysine hydrochloride,
N$^\alpha$-(S-acetyl-N-(3-acetylthio-2,2-dimethylproprionyl)-L-cysteinyl)-N$^\epsilon$-t-butoxycarbonyl-L-lysine,
N$^\alpha$-(S-acetyl-N-(3-acetylthio-2,2-dimethylpropionyl)-L-cysteinyl)-L-lysine methyl ester hydrochloride,
3-amino-N-(S-benzyl-N-(3-benzylthio-2,2-dimethylpropionyl)-L-cysteinyl)propylamine, 4-amino-N-(S-benzyl-N-(3-benzylthio-2,2-dimethylpropionyl)-L-cysteinyl)butylamine, 6-amino-N-(S-benzyl-N-(3-benzylthio-2,2-dimethylpropionyl)-L-cysteinyl)hexylamine 5-amino-N-(S-benzyl-N-(3-benzylthio-2,2-dimethylpropionyl)-L-cysteinyl)pentylamine, N,N'-bis(S-benzyl-N-(3-benzylthio-2,2-dimethylpropionyl)-L-cysteinyl)-1,5-diaminopentane and 5-hydroxy-N-(S-benzyl-N-(3-benzylthio-2,2-dimethylpropionyl)-L-cysteinyl)pentylamine.

* * * * *